United States Patent
Briggs et al.

(10) Patent No.: US 10,276,053 B2
(45) Date of Patent: Apr. 30, 2019

(54) COGNITIVE SYSTEM TO IMPROVE ATHLETIC PERFORMANCE WITH MOTIVATION FROM DIFFERENT TRAINING STYLES

(71) Applicant: International Business Machines Corporation, Armonk, NY (US)

(72) Inventors: Benjamin D. Briggs, Waterford, NY (US); Lawrence A. Clevenger, LaGrangeville, NY (US); Leigh Anne H. Clevenger, Rhinebeck, NY (US); Jonathan H. Connell, II, Cortlandt Manor, NY (US); Nalini K. Ratha, White Plains, NY (US); Michael Rizzolo, Albany, NY (US)

(73) Assignee: International Business Machines Corporation, Armonk, NY (US)

( * ) Notice: Subject to any disclaimer, the term of this patent is extended or adjusted under 35 U.S.C. 154(b) by 461 days.

(21) Appl. No.: 15/008,028

(22) Filed: Jan. 27, 2016

(65) Prior Publication Data
US 2017/0213470 A1  Jul. 27, 2017

(51) Int. Cl.
*G09B 5/12* (2006.01)
*A61B 5/11* (2006.01)
(Continued)

(52) U.S. Cl.
CPC .......... *G09B 5/125* (2013.01); *A61B 5/02055* (2013.01); *A61B 5/1118* (2013.01);
(Continued)

(58) Field of Classification Search
CPC ......... G09B 5/125; A61B 5/01; A61B 5/1118; A61B 5/4806
(Continued)

(56) References Cited

U.S. PATENT DOCUMENTS

| 7,786,856 B2 | 8/2010 | O'Brien |
| 8,086,421 B2 | 12/2011 | Case, Jr. et al. |

(Continued)

FOREIGN PATENT DOCUMENTS

EP  1737543 B1  12/2012

OTHER PUBLICATIONS

S. Lee, "Design Document for Development of Mining Minds Core Technology Exploiting Personal Big Data," (Project No. 10049079), Kyung Hee University, Apr. 24, 2015, 94 pages.

*Primary Examiner* — Robert P Bullington
(74) *Attorney, Agent, or Firm* — Vazken Alexanian; Michael J. Chang, LLC (57) ABSTRACT

Techniques for motivating a user during a workout using different coaching styles are provided. In one aspect, a method for motivational coaching of a user during workout sessions includes the steps of: selecting a coaching style for the user based on input from the user and from coaching styles used for at least one other user; determining, during a workout session, whether the coaching style should be changed to enhance performance of the user based on data obtained from the user via a mobile device worn by the user; changing the coaching style if it is determined that the coaching style should be changed to enhance performance of the user; continuing with a current coaching style if it is determined that the coaching style should not be changed; and providing feedback to the user during the workout session based on the coaching style.

18 Claims, 9 Drawing Sheets

(51) Int. Cl.
*A61B 5/00* (2006.01)
*A61B 5/0205* (2006.01)
*G09B 19/00* (2006.01)

(52) U.S. Cl.
CPC ............ *A61B 5/4806* (2013.01); *A61B 5/486* (2013.01); *G09B 19/0038* (2013.01); *A61B 5/681* (2013.01); *A61B 5/6898* (2013.01); *A61B 2560/0247* (2013.01)

(58) Field of Classification Search
USPC ........................................................ 434/247
See application file for complete search history.

(56) References Cited

U.S. PATENT DOCUMENTS

| | | |
|---|---|---|
| 8,162,804 B2 | 4/2012 | Tagliabue |
| 8,715,139 B2 | 5/2014 | DiBenedetto et al. |
| 8,944,959 B2 | 2/2015 | Chapa, Jr. et al. |
| 9,028,405 B2 | 5/2015 | Tran |
| 2007/0219059 A1 | 9/2007 | Schwartz et al. |
| 2010/0129780 A1 | 5/2010 | Homsi et al. |
| 2014/0081179 A1 | 3/2014 | Moore-Ede |
| 2015/0025997 A1* | 1/2015 | Tilenius ............. G06Q 30/0631 705/26.7 |
| 2015/0294595 A1* | 10/2015 | Hu ....................... G06Q 10/101 434/127 |
| 2015/0332606 A1* | 11/2015 | Orosco ............. G09B 19/0038 434/247 |

\* cited by examiner

100

```
┌─────────────────────────────────┐
│  Initial selection of coaching  │
│  style.                         │
│            102                  │
└─────────────────────────────────┘
```

```
┌─────────────────────────────────┐
│  Dynamic selection of coaching  │
│  style.                         │
│            104                  │
└─────────────────────────────────┘
```

```
┌─────────────────────────────────┐
│  Modulation of coaching style.  │
│            106                  │
└─────────────────────────────────┘
```

COGNITIVE SYSTEM TO IMPROVE ATHLETIC PERFORMANCE WITH MOTIVATION FROM DIFFERENT TRAINING STYLES

FIELD OF THE INVENTION

The present invention relates to coaching styles used to motivate a user during a workout, and more particularly, to techniques for motivating a user during a workout using different coaching styles using the sensing capabilities of wearable mobile technology, such as a smartwatch, to determine current performance levels and to select the best coaching style for the performance levels.

BACKGROUND OF THE INVENTION

Athletes constantly strive to perform at a higher level, run faster, longer, etc. To do so, they need to be able to assess their performance and identify areas for improvement.

Current solutions for athletes to analyze their performance passively report statistics. For instance, technology such as Fitbit® allows users to track their heart rate, number of steps taken, and other personal metrics.

However, merely monitoring statistics does not do much to motivate the user. For instance, merely knowing their current heart rate or distance they have run doesn't provide users much feedback to induce changes in their behavior that will bolster their performance.

Further, the motivation an athlete needs to improve his/her performance can vary over time. For instance, leading up to an event, e.g., a game, a race, a match etc., a certain training style might help motivate the athlete to best prepare for the event. However, during the event, a different approach may be beneficial to help the athlete to perform at his/her best. The feedback an athlete needs may even change during an event. For instance, during a marathon, feedback provided to a runner at the start of the race to motivate them may be different from that needed when they are a mile or so from the finish line.

Therefore, techniques for assessing performance that maximize the motivational benefit to an athlete and which can change based on changing conditions would be desirable.

SUMMARY OF THE INVENTION

The present invention provides techniques for motivating a user during a workout using different coaching styles leveraging the sensing capabilities of wearable mobile technology, such as a smartwatch, to determine current performance levels and to select the best coaching style for the performance levels. In one aspect of the invention, a method for motivational coaching of a user during workout sessions is provided. The method includes the steps of: selecting a coaching style for the user based on input from the user and from coaching styles used for at least one other user; determining, during a workout session, whether the coaching style should be changed to enhance performance of the user based on data obtained from the user via a mobile device worn by the user; changing the coaching style if it is determined that the coaching style should be changed to enhance performance of the user; continuing with a current coaching style if it is determined that the coaching style should not be changed; and providing feedback to the user during the workout session based on the coaching style.

A more complete understanding of the present invention, as well as further features and advantages of the present invention, will be obtained by reference to the following detailed description and drawings.

DETAILED DESCRIPTION OF PREFERRED EMBODIMENTS

Provided herein are techniques for giving athletes feedback on their performance and particularly to employing different training styles to motivate athletes based on their performance. Namely, it is recognized herein that the use of different training styles for different athletes can be useful in helping them achieve their best performance. Further, the training style that best motivates an athlete may change over time, or even during a given sporting event. For instance, a runner halfway through a marathon may be tired, and thus a more aggressive approach may be needed to motivate them as compared to when they first started the race and were full of energy.

Advantageously, the present techniques leverage the capabilities of wearable mobile smart technology, such as a smartwatch, to collect comprehensive data from a user and provide feedback to the user about their performance. The feedback is provided to the user using a variety of different training or coaching 'styles.' Traditionally, a coach or trainer is someone who works with an athlete to help the athlete maximize their performance. Different coaches/trainers might employ different approaches to motivate the athlete. These approaches are what are referred to herein as a coaching/training style. For instance, one style might use positive reinforcement and humor as motivation. Another might use a straightforward, goal-oriented approach. Athletes may respond differently to these various approaches. Further, their response may change over time and/or depending on the circumstances. Advantageously, the present techniques determine the best coaching style to use to motivate an athlete at any given time, and permit dynamic selection of different coaches as the situation warrants.

Figure 1:
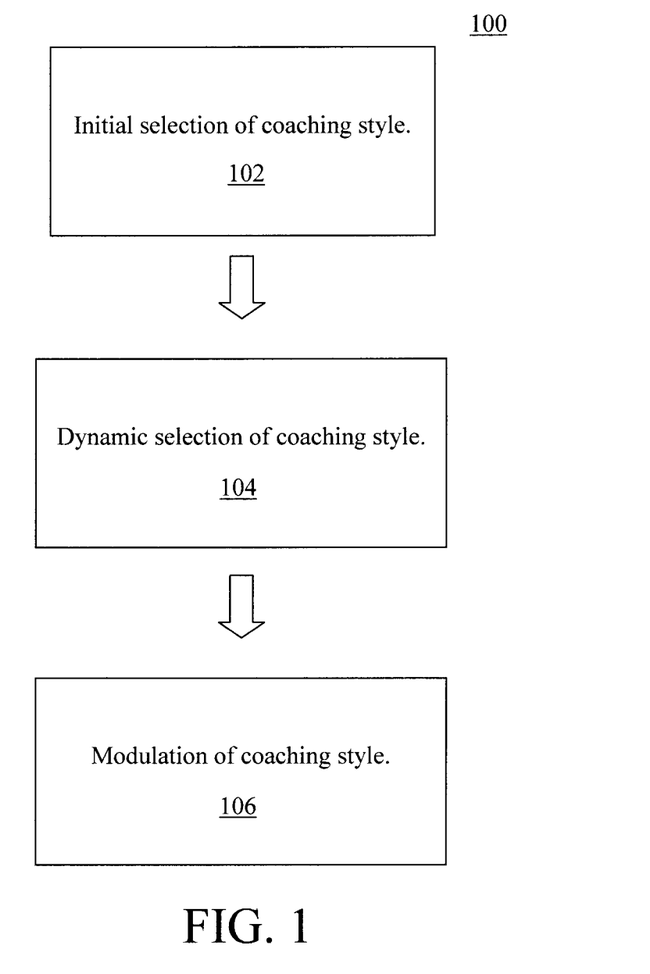
FIG. 1 is a diagram illustrating how the present process for motivational coaching includes three phases: an initial selection of coaching style phase, a dynamic selection of coaching style phase, and a modulation of coaching style phase according to an embodiment of the present invention.

An overview of the present techniques is now provided by way of reference to methodology 100 of FIG. 1. As shown in FIG. 1, the present motivational coaching involves three phases: Phase 102: the initial selection of coaching style, Phase 104: dynamic coaching style selection based on performance during an activity, and Phase 106: a modulation of coaching style based on changing life circumstances.

The initial selection of coaching style phase (Phase 102) is based on matching the athlete's demographics (i.e., statistical data) with those of others users of the system. The idea here is that the coaching style which works best for others could also work for you. After the initial coaching phase is selected, the user starts his/her workout.

The dynamic selection of coaching style phase (Phase 104) is programmed to run during a workout after a baseline fitness level has been determined using sensor data from the user's wearable mobile device, e.g., smartwatch. If the athlete is falling below the target, the athlete can choose to revise their initial data and/or goals (i.e., based on the sensor data) and rematch to a coach based on that new information, additional fitness and health data that was gathered on the athlete, and/or data from other users in the system. Alternatively, if the user does not want to revise their initial data and/or goals, a new coach can be chosen randomly.

The modulation of coaching style phase (Phase 106) is triggered by either a sensor or a query response which indicates an unusual circumstance, requiring a temporary change of coach for the session. For example, an unusual circumstance might be if the athlete has a cold (such as a fever detectable based on body temperature), the environmental sensors show unusual heat or cold, or sleep logs show lack of sufficient rest between workouts. After a weighted evaluation, this data could trend negative, indicating a change to a more conservative coach, or positive (a perfect day), indicating a change to a more aggressive coach. By way of example only, a conservative coach would have a more technical focus, motivating through explanations of theory, as opposed to an aggressive coach who would motivate using emotions.

In the description that follows, several different coaching styles will be used as non-limiting examples. A first coaching style used herein may be characterized as having a technical focus working with the entire body to create an optimal environment for healing and performance training. Another is an enthusiastic, positive coaching style, i.e., motivation through positive reinforcement. Yet another exemplary coaching style used herein is a more aggressive approach, i.e., don't let anything get in the way of accomplishing your goals.

Figure 2:
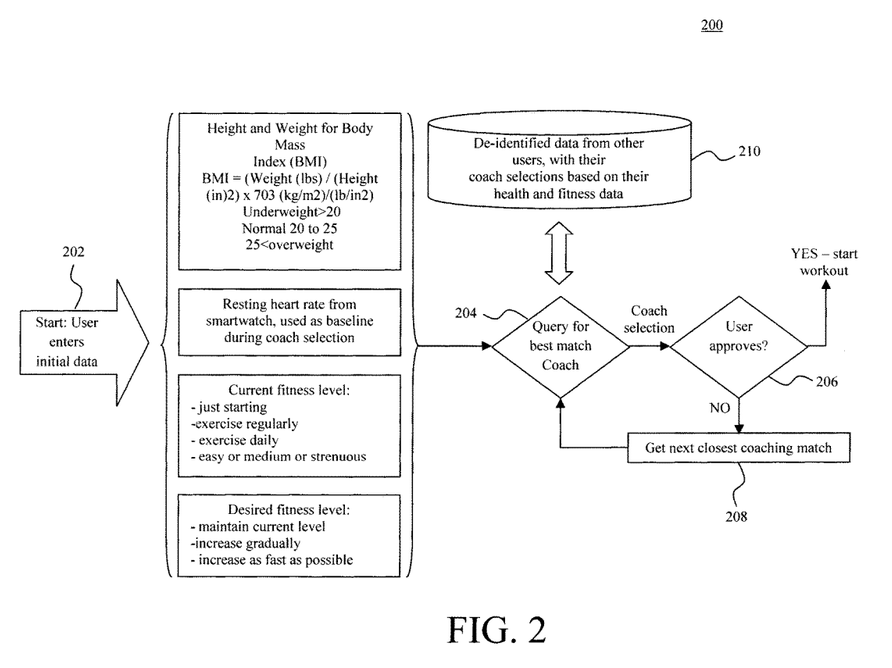
FIG. 2 is a diagram illustrating an exemplary methodology for performing the initial selection of coaching style phase of the present process according to an embodiment of the present invention.

A description of each of these three phases of the present process is now provided. For instance, FIG. 2 provides an exemplary methodology 200 for performing the first phase 104 of initial coaching selection. To begin the process, in step 202, initial data is obtained from the user. As highlighted above, the present process leverages mobile technology worn by the user, such as a smartwatch. Some of the initial data is obtained directly from the user via the user's mobile device and other initial data is entered by the user. The user can enter data into his/her smartwatch, or using a smartphone or personal computer linked to the user's smartwatch.

For example, in step 202, the user can enter his/her statistics, such as height and weight, current fitness level, and desired fitness goals. As shown in FIG. 2, data such as height and weight can be used to calculate the user's body mass index or BMI which indicates whether the user is under/overweight or normal. To indicate his/her current fitness level, the user might be provided with several categories from which he/she can make a selection that best indicates the user's current fitness level, such as "just starting," "exercise regularly," "exercise daily," and a degree such as "easy," "medium" or "strenuous" (e.g., the user can select that currently she exercises regularly at a medium level). Similarly, the user might be presented with several options from which he/she can pick the one that best describes his/her fitness goals, such as "maintain at current level," "gradually increase level," or "increase fitness level as fast as possible."

As will be described in detail below, current smartwatch technology includes a variety of different sensors equipped to obtain information from a user and/or from the user's surroundings. This sensor technology is leveraged herein to obtain initial data from the user. For instance, in the present example, the user's smartwatch may be used to obtain vitals from the user such as the user's heart rate. As will be described in detail below, the user's heart rate may be one parameter used in selecting the proper training coach for the user.

The next task is to determine a proper coaching style for the user. According to an exemplary embodiment, the initial data for the user is compared with that of other users with similar demographics, and a coaching style is suggested for the user based on what the other users have chosen. The user will then be given a choice to stick with the suggested coaching style, or pick another.

Specifically, in step 204 a query is made (e.g., against a database 210 of users) as to the best match coach. For instance, database 210 can include users' health and fitness data and the corresponding coaching style selection. For privacy aspects, the data preferably is not identifiable with a specific user (i.e., de-identified) but merely associates a specific coaching style with certain health and fitness statistics. To use a simple example to illustrate the query performed in step 204, say the user entered as initial data that she has a BMI of 24, her current fitness level is exercise daily, and her goal is to increase her fitness level gradually. The coaching style query then matches this initial data with that in database 210 to see what type of coaching style other users with the same (or similar) statistics have chosen. Say for example in this case that 20 others in the database 210 with the same statistics as the user chose a technical coaching style and 2 chose an aggressive coaching style. Then the logical approach would be to first try the most popular choice (technical) for the user. The next best match would be aggressive should the user want to change styles. If there is not another user with all of the same statistics, then the match can be based on the other user(s) having the greatest number of matching statistics, and so on.

Based on the query performed in step 204 against the database 210, a coaching style is suggested for the user. In step 206, the user is given the chance to approve the suggested coaching style. For instance, using the example above, if a technical approach is suggested for the user, but the user feels she would benefit more from an aggressive training style, then the user can in step 206 reject the choice.

If the user rejects the coaching style suggested for them, then in step 208 the next closest coaching match is selected for the user (based on the next best match from the database 210—see above). The user can evaluate the next best match (as per step 206) and the process can be repeated until an acceptable coaching style is presented to the user. When the user approves a coaching style, then the user can start her workout. This concludes the initial coaching style selection phase.

It is notable that the health and fitness data for the users of the present process are stored in database 210, and are updated as the users perform workout sessions. As will be described in detail below, this data will be used throughout the process to update coaching styles and fitness goals. For instance, in the second phase of the process (phase 104: dynamic selection of coaching style), the fitness level and fitness level goals of the user after a workout has begun can be compared with the statistics of other users to see whether a change in coaching style is warranted. By way of example only, the health and fitness data can include metrics such as number of sit-ups or push-ups each user can perform, how far they can run without stopping, etc. If, based on these metrics, a user is under/overperforming as compared to other users in the database, then a change in coaching style might be needed to further bolster performance.

Figure 3:
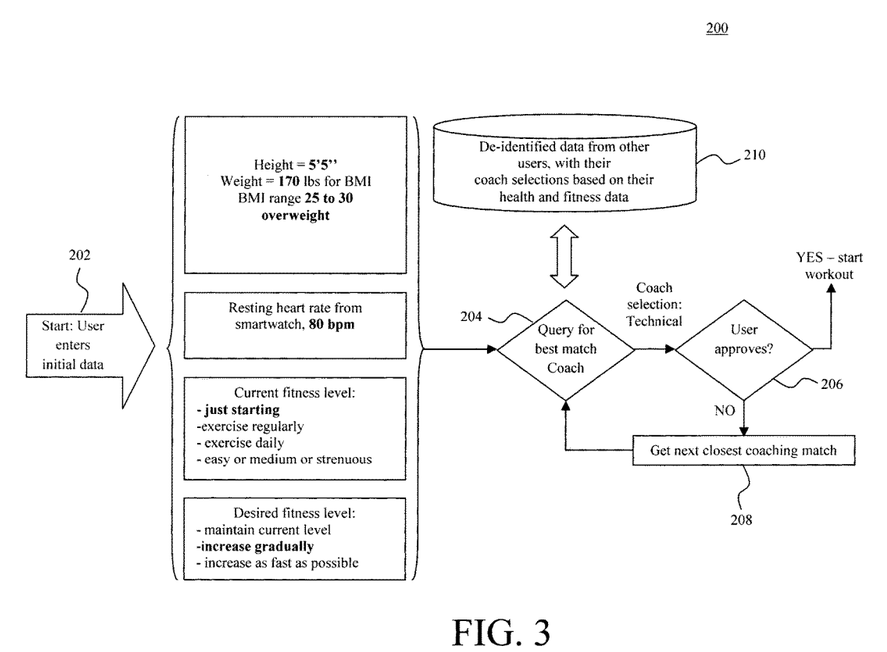
FIG. 3 is a diagram illustrating an example of the initial selection of coaching style phase of the present process according to an embodiment of the present invention.

By way of example only, FIG. 3 provides an exemplary implementation of methodology 200 for a given user. FIG. 3 is meant merely to provide a non-limiting illustrative example. In this example, the initial data obtained from the user in step 202 is that the user's height is 5 feet, 5 inches and has a weight of 170 pounds (which equates to a BMI of 25 to 30). The user indicates that his/her current fitness level is "just starting" and that his/her fitness level goal is to "increase gradually." It is also determined from the user's smartwatch that he/she has a resting heart rate of 80 beats per minute (bpm).

From this initial data, a query is made in step 204 against the database of other users 210 (as described above) and it is determined that the coaching style best matched to the user is technical. The user can then approve of the suggested coaching style in step 206, or ask for the next best match in step 208, in the manner described above, until a suitable match to the user is provided. Once the user approves of a coaching style match, then the user can begin his/her workout.

As provided above, the next phase in the present process is the dynamic selection of coaching style phase where, during a workout, the coaching style can be revised to best conform to the user's workout performance. In this phase, if the user is falling below his/her target, the user can revise their initial data (e.g., change the fitness goals). Data can also be collected from the user (e.g., via the user's smartwatch) and/or from other users to help select a different coaching style to help maximize performance.

Figure 4:
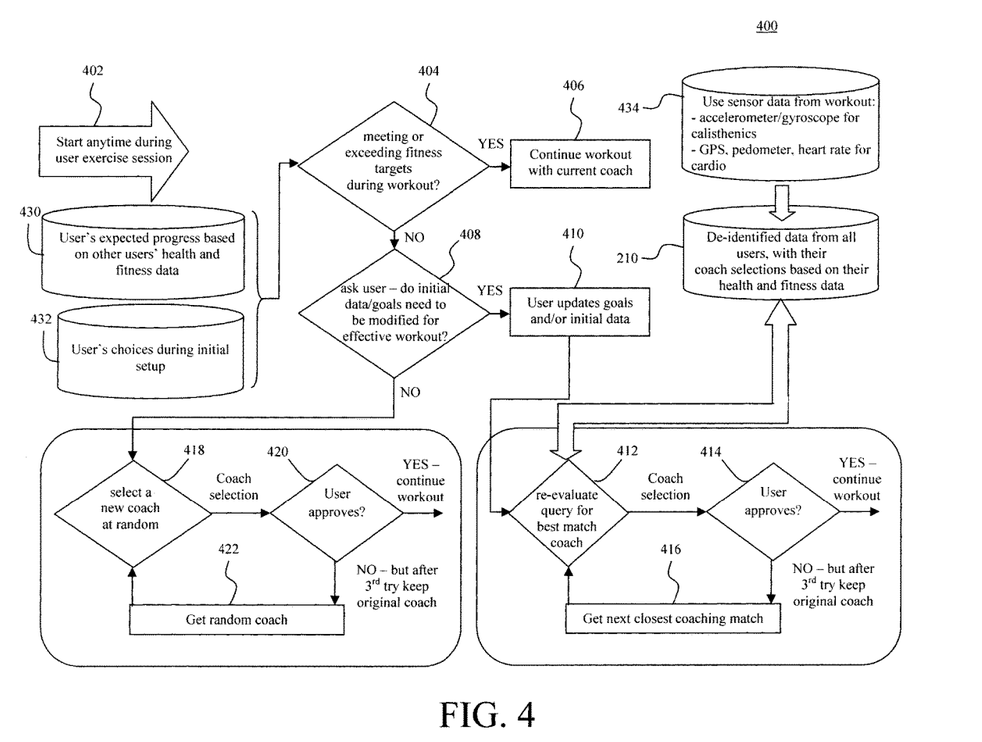
FIG. 4 is a diagram illustrating an exemplary methodology for performing the dynamic selection of coaching style phase of the present process according to an embodiment of the present invention.

FIG. 4 provides an exemplary methodology 400 for performing the second phase 104 (see FIG. 1) of dynamic selection of coaching style during a workout. The dynamic selection process begins in step 402 anytime during an exercise session, wherein the user's current coaching style and desired fitness level goals data (from the first phase 102), as well as health and fitness data from other users (i.e., from database 210) are obtained. As provided above, the health and fitness data may include metrics such as the number of sit-ups/push-ups each user can do, the distance each user can run without stopping, etc.

In step 404, a determination is made as to whether the user is meeting or exceeding their expected fitness targets during the workout. According to an exemplary embodiment, the expected fitness targets for a user are based on a comparison with the health and fitness statistics of other users. For instance, if after 2 weeks users with comparable statistics are able to do 20 push-ups but the user is only able to do 10, then the user has not met the expected fitness target. On the other hand, if the user meets (or exceeds) his/her expected fitness targets then same coach is kept, as that is working well for them and thus there is no need to change. As provided above, comparable users might be those having the same or similar vitals, i.e., height, weight, and/or the same or similar fitness goals. The data relating to the user's expected progress based on other users' health and fitness data, and to the user's choices during the initial set up are shown in FIG. 4 as being stored in databases 430 and 432, respectively, however this data can also be stored generally as health and fitness data in database 210.

If it is determined in step 404 that the user has met or exceeded these fitness goals, then it is assumed that the current coaching style is working for them. In that case, the user will continue in step 406 with the current workout coach. The process can, however, be repeated at regular intervals, e.g., at least once during each workout session, once a week, once a month, etc. and/or when unusual circumstances occur (as per the third phase).

On the other hand, if in step 404 it is determined that the user has not met the expected fitness goals, then further steps may be taken to try and help the user achieve maximum performance. These steps can involve modifying the coaching style to better suit the user. The modifications of coaching style can be made based on updates to the initial data/fitness goals by the user him/herself, or automatically (e.g., by the system randomly selecting a new coach for the user). For instance, in step 408 the user (who is not meeting expected fitness goals) is queried as to whether he/she thinks that the initial data and/or fitness goals (the user provided in the first phase) should be updated to get a more effective workout. If the user thinks that such updates would be useful, then the process proceeds in a manner similar to the first phase, except this time with real-time fitness data from the user's current workout. For example, in step 410 the user updates his/her fitness goals (see above) and/or initial data. For instance, the user's weight may have changed since the initial data was last entered and/or the user may now want to change his/her expectations. Based on the updated data from the user (from step 410), in step 412 the system re-evaluates the query for best match coach for the user. As described above, this process involves comparing the user's data against the health and fitness data and goals of other users, e.g., in database 210. Here, sensor data from the user's workout is also taken into account. This data is shown in FIG. 4 as being stored in a database 434, however the user's sensor data can also be stored as health and fitness data in database 210. The sensor data represents generally any data that can be obtained from the user via his/her wearable mobile device (i.e., smartwatch) during a workout. By way of example only, the sensor data can include accelerometer and/or gyroscope data for detecting movement during calisthenics (i.e., number of sit-ups, push-ups, etc.), global positioning system (GPS), pedometer, and/or heart rate data for cardio exercise, etc. Thus, as compared with the initial selection from the first phase, here the coach selection process has more data for the user's current capabilities. For instance, the other users against which the current user is compared might now be those having the same/similar sensor metrics, along with similar vitals and fitness goals. A coaching style can then be selected for the user based on the coaching style used for others having similar metrics.

The user is again given the choice in step 414 to approve the coach selection, or to have another next closest coaching match selected in step 416. While the selection process can be iterated until the user finds a suitable coaching style match, it is preferable that a limit be set on the number of different matches that can be tried before the system defaults back to the current coaching style. Since the second phase is performed during a workout, setting a limit prevents excessive delays during the workout. By way of example only, a limit of 3 attempts can be set, before the system defaults back to the current coach.

With regard to coaching styles, as provided above these can include for example technical (conservative), enthusiastic and aggressive styles. Other possible coaching styles could include a specific athletic focus (e.g., soccer, skiing, or Tai Chi coach, etc.). Additionally, users might be given an option (for instance during setup) to add their own custom coaching style using a coaching template.

If, however, in step 408 the user chooses not to update their initial data or fitness goals, then the process attempts to select a new coach at random and to see if that new selection is suitable to the user. For instance, in step 418 the system selects a new coach at random which the user can either approve in step 420, or another, different random coach is selected in step 422. In the same manner as described above, the process can be repeated until a suitable (randomly selected coach in this case) is found. However, in order to prevent excessive disruption to the workout, a limit on the number of attempts (e.g., 3 times) is preferably set.

Figure 5:
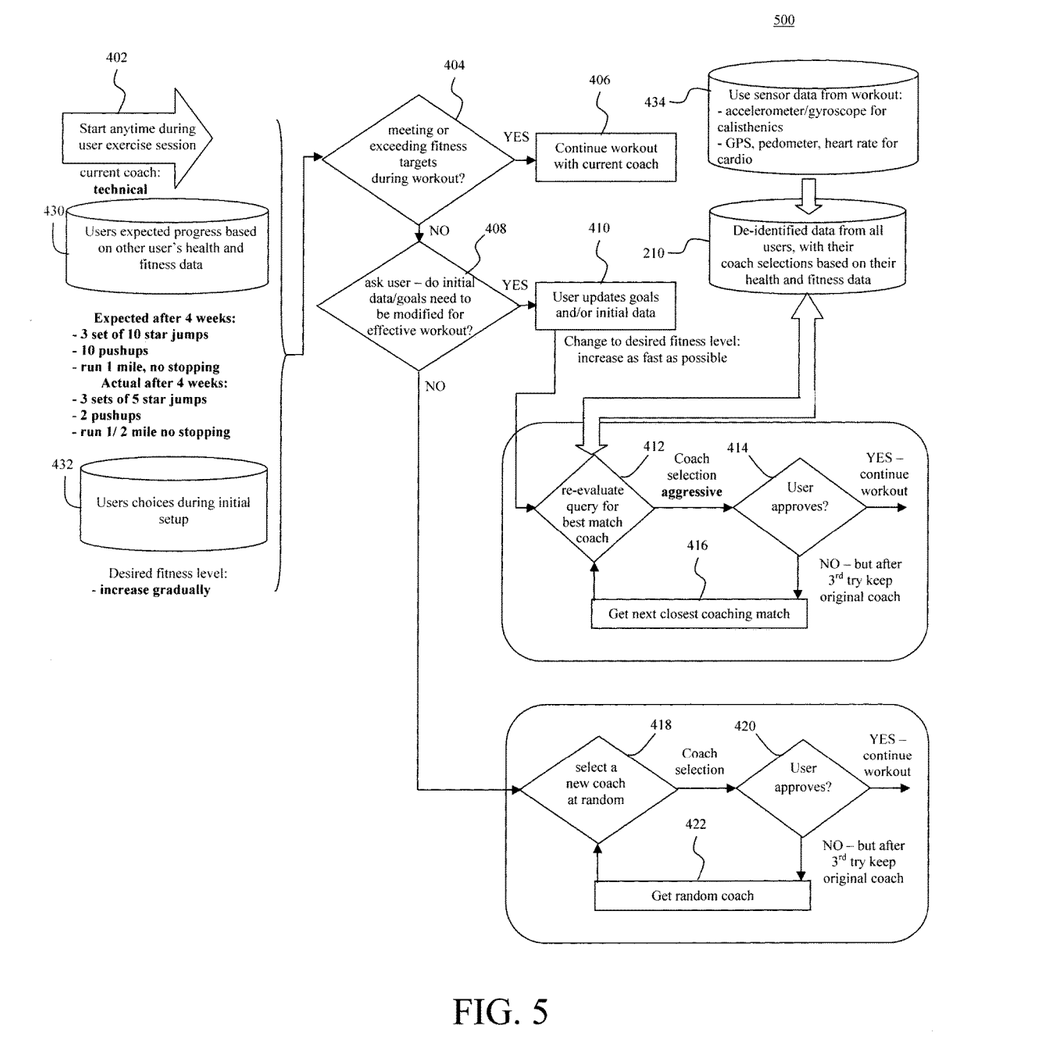
FIG. 5 is a diagram illustrating an example of the dynamic selection of coaching style phase of the present process according to an embodiment of the present invention.

FIG. 5 provides an exemplary implementation of methodology 400 for the dynamic selection of coaching style during a workout (second phase) for a given user. FIG. 5 is meant merely to provide a non-limiting illustrative example. In this example, the current coaching selection during the workout is "technical" and the user is not quite meeting his/her expected fitness targets. Namely, in the manner described above, based on the progress of others with similar statistics and coaching style, after 4 weeks of the program the user is expected to be able to do 3 sets of 10 star jumps, 10 push-ups, and run 1 mile without stopping. However, during the current workout (which is at the 4 week mark) the user is only able to do 3 sets of 5 star jumps, 2 push-ups, and can only run ½ mile without stopping (see database 430). The user's initial fitness level goals were set as "increase gradually" (see database 432).

In this case, the assessment made in step 404 might be that the user is not meeting the expected fitness targets during the workout (i.e., the user is not performing in his/her current workout to the level expected), and in step 408 the user is given the opportunity to update his/her initial data and/or fitness goals. If the user chooses to update his/her initial data and/or goals, then that data can be re-evaluated (in step 412)—this time in light of fitness sensor data collected, e.g., via the user's smartwatch, a new coach selection made (in this example "aggressive"—e.g., which may help further motivate the user to meet his/her fitness goals), and the user's approval sought (in step 414). The process can be iterated until a suitable coach is selected. However, a limit on the number of tries is preferably set to avoid excessive disruption to the workout (with the default being to go back to the original selection).

To aid the user in approving/disapproving a particular coaching style, the process would provide a short description of why the change is suggested, for example if a specific goal for heart rate is not met, and a few important characteristics of the new coach, such as, "the recommended coach would provide more detailed instructions for you to successfully complete the workout" or "the recommended coach will give you emotionally charged instructions to push your heart rate higher."

If the user chooses not to update his/her data or goals, then the above-described random coach selection process can be implemented as per steps 418-422. Again, it is preferable to set a limit on the number of attempts to pick a random coach suitable to the user before the system defaults back to the current coach.

As provided above, the third phase in the present process is the modulation of coaching style phase where unusual circumstances during a particular workout are present (e.g., the user has a cold, the weather is extremely hot or cold, etc.) and are affecting performance. The notion here is that while the current coaching style might be generally appropriate for the user, unusual circumstances during a particular session might warrant a temporary change in approach to help the user maximize his workout performance. For instance, as will be described in detail below, sensor data (e.g., from the user's smartwatch) can be used to determine whether the user might be exhibiting unusual characteristics, such as a fever (the user is not feeling well), the user has not had enough sleep, is stressed, etc., and/or that there are unusual environmental factors, such as extreme temperatures, high humidity, wind, etc.—all of which might contribute to the user having an unusually good or bad workout.

Figure 6:
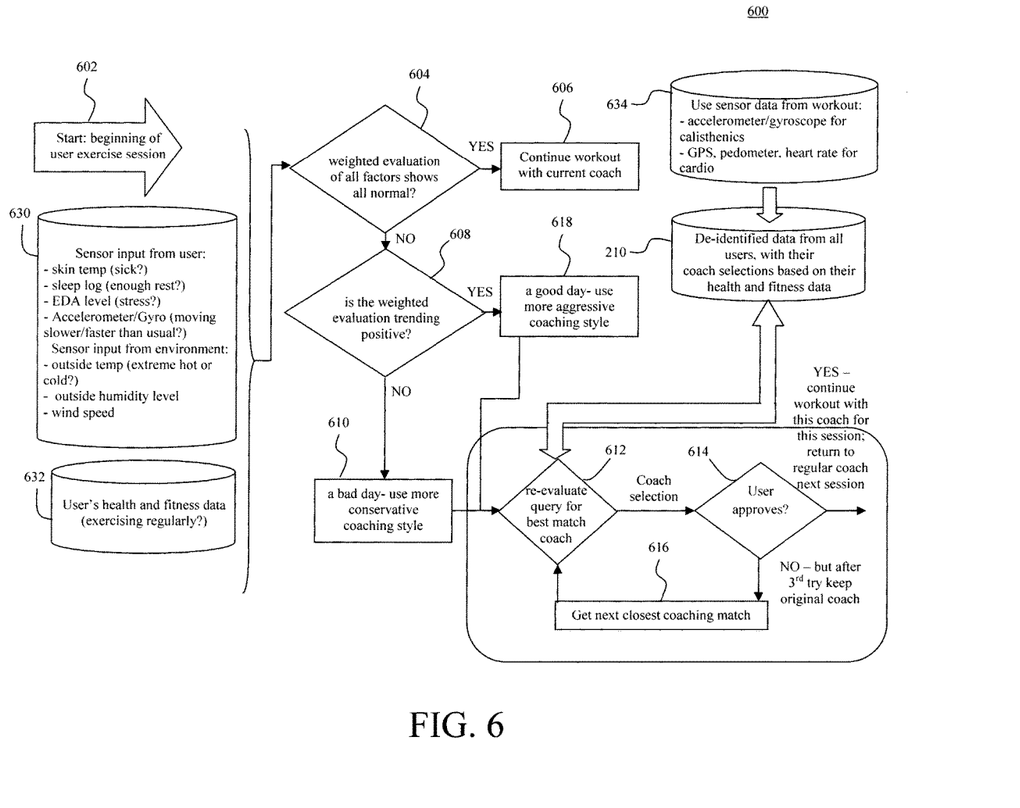
FIG. 6 is a diagram illustrating an exemplary methodology for performing the modulation of coaching style phase of the present process according to an embodiment of the present invention.

FIG. 6 provides an exemplary methodology 600 for performing the third phase 106 (see FIG. 1) of modulating coaching style at the beginning of a workout session. The coaching modulation process preferably begins in step 602 at the beginning of an exercise session, wherein sensor data from the user is obtained (e.g., via the user's smartwatch) as is the health and fitness data stored for the user. The sensor data, and the user's choices during the initial set up are shown in FIG. 6 as being stored in databases 630 and 632, respectively, however this data can also be stored generally as health and fitness data in database 210. Throughout the process the sensor data is evaluated as it is gathered, and then stored in the database for reference when past health history needs to be evaluated. Storing the sensor data provides a basis for evaluating whether the user is having an (unusually) good or bad workout. For instance, using the example provided in FIG. 6, the sleep log can indicate (based on past data stored in database 630) that the user has had less or more sleep than usual. Similarly, accelerometer and gyroscope sensor data can indicate that the user is moving slower or faster than usual. Environmental extremes can also be identified based on data collected in the past to establish what is typical and what is out of the ordinary or unusual.

Based on the sensor data, in step 604 a weighted evaluation of the factors is made to determine whether all is normal, or if unusual circumstances are present. For instance, if the user has an elevated temperature, it is unseasonably warm or cold, etc. this might indicate that unusual factors are present. A weighted evaluation means that not all factors are taken into account equally. Weighting will be individualized, depending on the user's fitness goals and health history. For example, if the process has been told that a user enjoys running only in 30° F. to 50° F. temperatures, for them low temps would be weighted lightly, and higher temps weighted heavily.

If it is determined in step 604 that all the sensor data appears normal, then in step 606 the user will continue with his/her current coach. Another evaluation may be performed at the beginning of the next workout. On the other hand, if the sensor data is unusual, then a determination is made in step 608 as to whether the effect on the user's workout performance during this session is positive or negative. For instance, if the user is feeling unwell (e.g., has a temperature) or has a lack of sleep his/her performance can be negatively affected. The user's performance for a given workout session can be easily ascertained based on the sensor data according to the above-described metrics such as accelerometer/gyroscope for determining the number of calisthenics performed; GPS, pedometer, heart rate sensor for cardio performance, etc. On the other hand, the unusual circumstances might actually boost performance. For instance. cooler weather might permit the user to run farther and faster before tiring. In either case, it may be desirable to evaluate whether a change in coaching style for this particular workout session might benefit the user's performance given the special circumstances.

For instance, if it is determined in step 608 that the user is having a bad day (i.e., the evaluation is trending negative), then in step 610 a switch to a more conservative coaching style is implemented. This updated coaching style is selected in the same general manner as described in accordance with the description of the second phase above. Namely, in step 612 the system re-evaluates the query for best match coach for the user. As shown in FIG. 6, this process involves comparing sensor data from the user's current workout against the health and fitness data and goals of other users, e.g., in database 210. This data is shown in FIG. 6 as being stored in a database 634, however the user's sensor data can also be stored as health and fitness data in database 210. The sensor data represents generally any data that can be obtained from the user via his/her wearable mobile device (i.e., smartwatch) during the current workout. A coaching style can then be selected for the user based on the coaching style used for others having similar metrics to those of the user on his/her bad day.

The user is given the choice in step 614 to approve the coach selection, or to have another next closest coaching match selected in step 616. As above, it is preferable that a limit be set on the number of different matches that can be tried before the system defaults back to the current coaching style so as to prevent excessive delays during the workout. If/when the user approves a coaching style change, then that updated coach is implemented only for the current workout session since it is assumed that the user will return to his/her usual form in subsequent workouts. Thus, the updated coach selection is applied only for the current workout session, after which the system reverts back to the regular coach for the user (i.e., the coach selection as per the first and second phases when unusual circumstances are not present).

In the case where it is determined in step 608 that the user is having a good day (i.e., the evaluation is trending positive), then in step 618 a switch to a more aggressive coaching style is implemented. The same process is implemented via steps 612-618 as described above, however here the sensor data from the user would indicate a positive performance.

Figure 7:
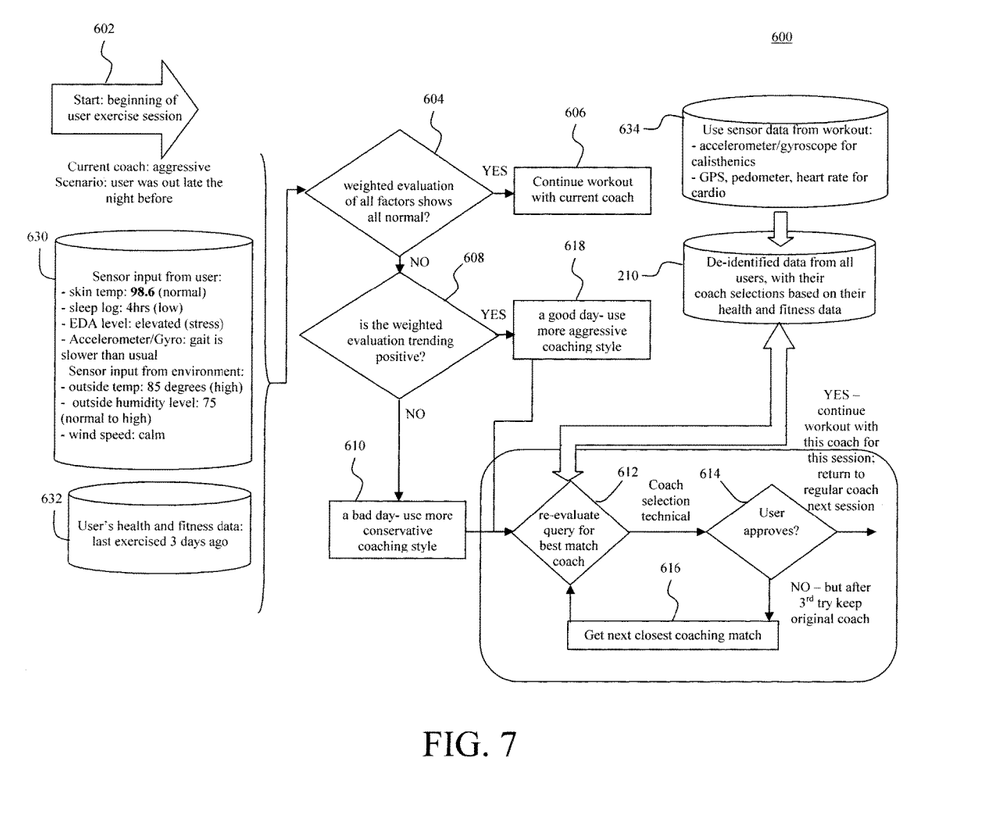
FIG. 7 is a diagram illustrating an example of the modulation of coaching style phase of the present process according to an embodiment of the present invention.

FIG. 7 provides an exemplary implementation of methodology 600 for the modulation of coaching style during a workout (third phase) for a given user. FIG. 7 is meant merely to provide a non-limiting illustrative example. In this particular example, the user is having an uncharacteristically bad day and the coaching style for this particular workout session is changed accordingly to a more conservative style.

As shown in FIG. 7, the user starts his/her workout with an aggressive style coach. However, data gathered in step 702 from the user (e.g., via the user's smartwatch) indicates that the user has a normal temperature (98.6 degrees), but the user had only 4 hours of sleep the night before, has an elevated stress level, and a gait that is slower than usual. The data also indicates that the outside temperature is high (85 degrees), and that there is a normal to high level of humidity. The user's health and fitness data indicates that the user last exercised 3 days before.

When a weighted evaluation of all of these factors is performed in step 604, it is determined in step 608 that the data trends negative, i.e., the user is having a bad day, and in step 610 a more conservative coaching style is selected for the user. Had the data indicated that the user's performance was normal then, as per step 606, the current coach would be maintained, or trending positive then, as per step 618, a more aggressive coaching style might be selected.

In this example, the re-evaluation process performed as per steps 612-616 suggests a more technical coach and, if the user approves the selection, this coaching style would be implemented solely for this particular workout session (after which the regular coach is reinstated).

It is notable that while described generally as first, second, and third, the above described phases of the present process can be performed in any order and/or can be iterated as needed based on changing conditions. For instance, dynamic coaching style selection (the second phase) can be performed at some point during each workout session, whereas the coaching modulation (third phase) may be performed only when the data (collected, e.g., at the beginning of a particular session) indicates unusual parameters. When the user's overall performance falls below target, then the initial selection process (first phase) can be repeated with updated data, goals, etc. from the user. Thus, each phase can be performed dynamically throughout the process, when needed, and with updated data to account for changing conditions.

In the examples above, sensor data is collected from the user via a wearable mobile device, such as a smartwatch. The present techniques can be implemented with any wearable technology (e.g., smartwatch, smartglasses, etc.) capable of directly acquiring real-time data from a user. Smartwatches which may be used in accordance with the present techniques are available from companies such as Motorola™ (e.g., the MOTO 360), Samsung™ (e.g., Samsung Gear™), Apple™ (e.g., the Apple Watch™), etc.

A non-exhaustive list of smartwatch capabilities that may be leveraged in accordance with the present techniques is now provided. Different smartwatches (or other suitable wearable technology) have different capabilities, such as a variety of different sensors, user interactive features such as voice commands, audible/motion alarms/alerts, etc. By way of example only, some of the smartwatch technology that may be leveraged for the present techniques includes the following:

Sensors—the present techniques envision use of one or more sensors proximate to the user (also referred to herein as proximal sensors). These are sensors that can measure physical/physiological conditions of the user. These types of sensors generally require contact with the user to function, and thus are also referred to herein as contact sensors. For instance, one such contact sensor is an electrodermal activity or EDA sensor. EDA sensors measure the electrical characteristics of the skin. The electrical characteristics of the skin are controlled, at least in part, by the state of sweat glands in the skin, which in turn are regulated by the sympathetic nervous system. Thus, EDA sensors can gauge sympathetic and nervous responses.

More specifically, based on a sweat gland circuit-loop, EDA measures strength of change in skin conductance to electrical charge as reflecting sympathetic nervous system response to sensation. This change is associated with eccrine sweat-gland activity innervated by the sympathetic branch of the autonomic nervous system. Reactions cannot be controlled instantly with the mind, thus measurements reliably record stress caused by external stimuli.

EDA data is classified as either tonic—low amplitude, low frequency waveforms typical in a relaxed state—or phasic—higher amplitude, higher frequency waveforms occurring 1 to 3 seconds after a sensory stimulus. This phasic measurement is the skin conductance response (SCR). Sensory stimulus can be auditory, visual, olfactory, tactile, or vestibular (vertigo, imbalance).

Stress can affect a user's workout session and/or coaching style which the user best responds. For instance, a user under stress from demands at work or school might underperform when an aggressive coaching style is used, and may respond better to an update to a conservative coach, such as a technical or positive reinforcement coaching style. Thus, in the context of the present techniques, EDA sensors can be used to collect real-time data indicating a level of stress of the user.

Other contact sensors useful for the present techniques include pulse oximeters and heart rate sensors. A pulse oximeter measures a person's blood oxygen levels often via a sensor placed on a part of the body such as a fingertip. Similarly, a heart rate sensor measures a person's heart rate or pulse (generally in beats per minute), e.g., via a sensor placed on the chest or wrist. As described above, the user's heart rate sensor data can help evaluate cardio performance. For instance, a user performing cardio exercises such as running often target a certain heart rate. Thus, a heart rate sensor can help assess whether the user has achieved this target.

Other useful proximal sensors are trajectory and pose sensors. For instance, as highlighted above, an accelerometer can be used to detect the user's movement, speed and direction. A gyroscope sensor (often used in conjunction with an accelerometer) detects direction or orientation. The accelerometer and gyroscope can be used to assess the user's performance during calisthenics, e.g., how many push-ups or sit-ups the user has done, etc. A rate gyroscope similarly measures the rate of change of angle with time. A global positioning system or GPS provides location information, e.g., distance covered during a run.

Sensors that detect movement can also be used to detect sleep trends. For instance, periods of non-movement or movement characteristic of sleep (e.g., briefly rolling over) can be deemed as time the user is sleeping. Movement and activity are indicative of awake behaviors. Thus, the present techniques can leverage the number of hours the user has slept, in determining whether an unusual situation is present and/or selection of the proper coaching style.

Yet another type of sensor that is useful for the present techniques is an environmental sensor. For instance, a compass and/or a magnetometer (which measures the direction of magnetic fields) can be used to determine the physical position of the user. A barometer, air temperature sensors, wind speed sensors, humidity sensors, etc. can be used to assess environmental conditions such as air pressure, temperature, wind velocity etc. As provided above, environmental factors such as temperature, humidity, wind, etc, can all contribute to a user's performance during a workout.

Figure 8:
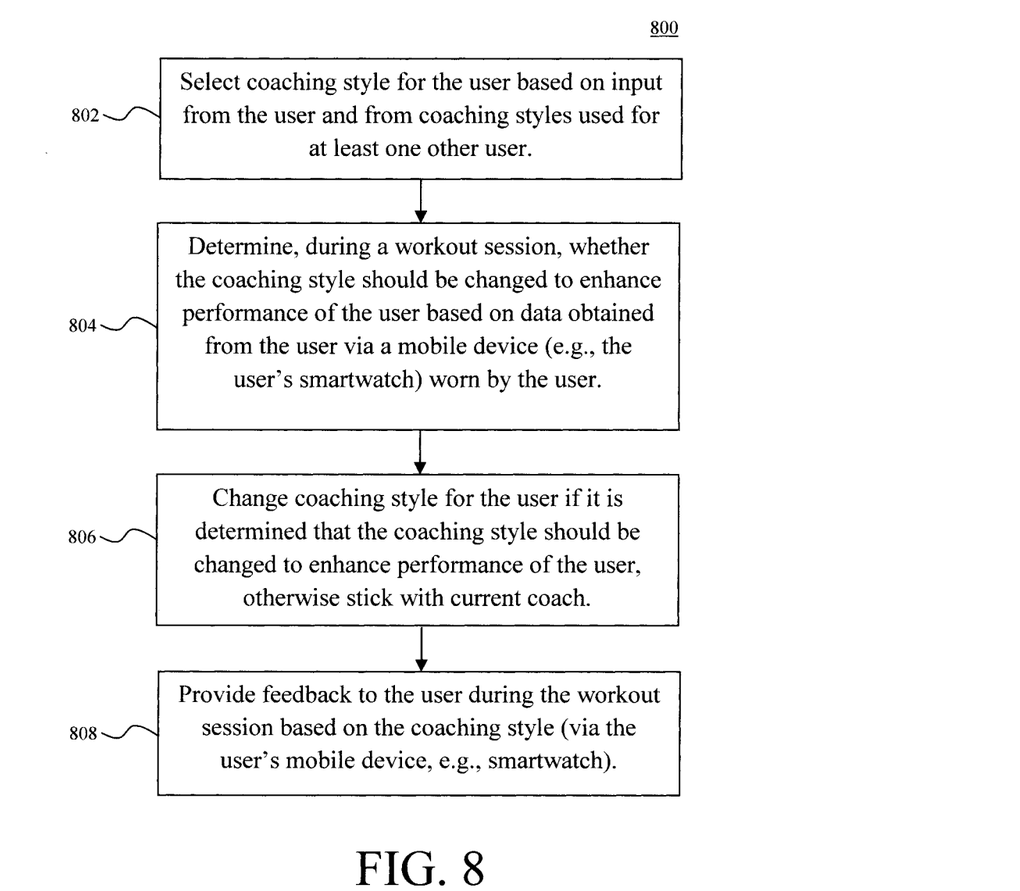
FIG. 8 is a diagram illustrating an exemplary methodology for motivational coaching of a user during workout sessions according to an embodiment of the present invention.

Based on the above-description of the phases used in the present process to select an appropriate workout coaching style for a user, FIG. 8 provides an exemplary methodology 800 for motivational coaching for a user during workout sessions. It is notable that the present techniques may be implemented to obtain user data and provide feedback to the user (according to the selected motivational coaching style) by way of the user's wearable mobile device (i.e., smartwatch).

In step 802, a coaching style is selected for the user based on input from the user and from coaching styles used for at least one other user. The process for selecting a coaching style for the user (e.g., an initial coaching style in the first phase and/or dynamic or modulated coaching styles in the second and third phases) was described in detail above.

In step 804, during a workout session, it is determined (as detailed above) whether the coaching style should be changed to enhance performance of the user based on data obtained from the user via a mobile device (e.g., the user's smartwatch) worn by the user. As highlighted above, this data can include for example: the user's temperature (e.g., does the user have a fever), sleep data from the user (e.g., has the user had enough sleep), user movement data (e.g., to assess performance during calisthenics), and combinations thereof. The data can also include environmental data such as: outside temperature, humidity, wind speed, and combinations thereof.

In step 806, the coaching style for the user is changed if it is determined that the coaching style should be changed to enhance performance of the user. The process for determining when the coaching style should be changed, and if so how, was described in detail above.

In step 808, feedback is provided to the user during the workout session based on the coaching style. According to an exemplary embodiment, the feedback is provide to the user via the user's wearable mobile device. For instance, messages can be provided to the user on their smartwatch in the form of text and/or audible messages or alerts. These messages will reflect the current coaching style selection. For example, an aggressive coaching style may result in a message such as "you are slacking, run faster!", "you are not trying hard enough, put more effort into it", etc. A more conservative, e.g., technical, style might be "you need to concentrate on your arm movements", "you are doing well with your cardio workout, but now we need to focus on your strengthening routine", etc.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Figure 9:
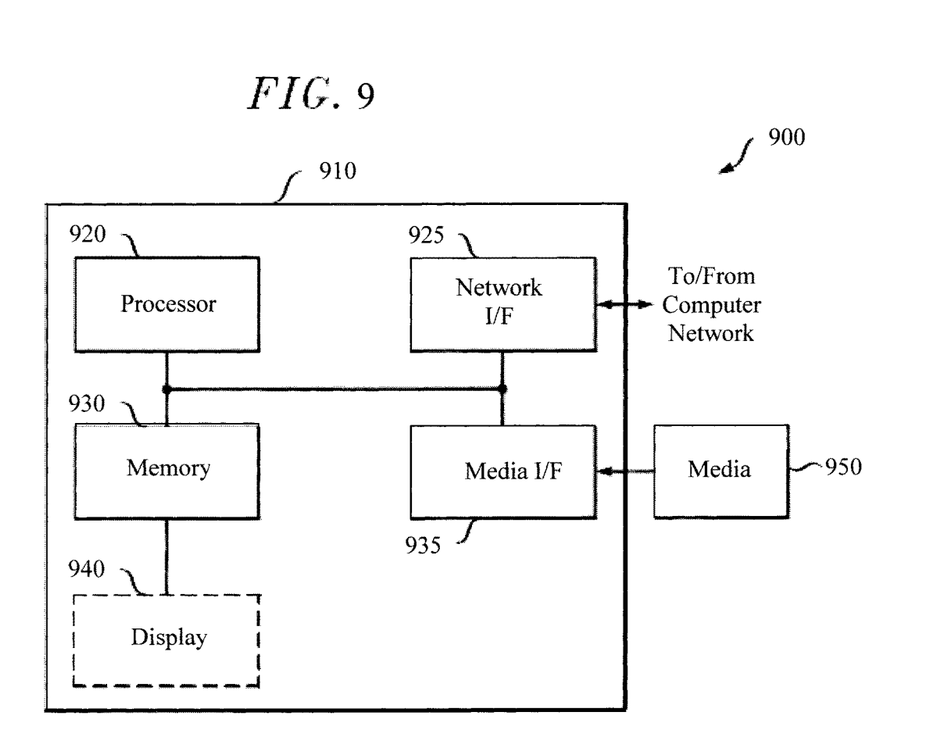
FIG. 9 is a diagram illustrating an exemplary apparatus for performing one or more of the methodologies presented herein according to an embodiment of the present invention.

Turning now to FIG. 9, a block diagram is shown of an apparatus 900 for implementing one or more of the methodologies presented herein. For example, apparatus 900 can be configured to implement one or more of the steps of methodology 100 of FIG. 1, methodology 200 of FIG. 2, methodology 400 of FIG. 4, methodology 600 of FIG. 56, and/or methodology 800 of FIG. 8.

Apparatus 900 includes a computer system 910 and removable media 950. Computer system 910 includes a processor device 920, a network interface 925, a memory 930, a media interface 935 and an optional display 940. Network interface 925 allows computer system 910 to connect to a network, while media interface 935 allows computer system 910 to interact with media, such as a hard drive or removable media 950.

Processor device 920 can be configured to implement the methods, steps, and functions disclosed herein. The memory 930 could be distributed or local and the processor device 920 could be distributed or singular. The memory 930 could be implemented as an electrical, magnetic or optical memory, or any combination of these or other types of storage devices. Moreover, the term "memory" should be construed broadly enough to encompass any information able to be read from, or written to, an address in the addressable space accessed by processor device 920. With this definition, information on a network, accessible through network interface 925, is still within memory 930 because the processor device 920 can retrieve the information from the network. It should be noted that each distributed processor that makes up processor device 920 generally contains its own addressable memory space. It should also be noted that some or all of computer system 910 can be incorporated into an application-specific or general-use integrated circuit.

Optional display 940 is any type of display suitable for interacting with a human user of apparatus 900. Generally, display 940 is a computer monitor or other similar display.

Although illustrative embodiments of the present invention have been described herein, it is to be understood that the invention is not limited to those precise embodiments, and that various other changes and modifications may be made by one skilled in the art without departing from the scope of the invention.

What is claimed is:

1. A method for motivational coaching of a user during workout sessions, the method comprising the steps of:
   selecting a coaching style for the user based on input from the user and from coaching styles used for at least one other user;
   querying the user as to whether the user approves of the coaching style selected for the user;
   selecting a different coaching style if the user disapproves of the coaching style selected for the user;
   determining, during a workout session, whether the coaching style should be changed to enhance performance of the user based on data obtained from the user via a mobile device worn by the user, wherein the mobile device worn by the user comprises at least an electrodermal activity (EDA) sensor that collects the data from the user in real-time indicating a level of stress of the user, and an accelerometer and a gyroscope sensor that collect the data from the user in real-time indicating movement of the user, wherein the level of stress of the user and the movement of the user are factors that affect the performance of the user and whether the coaching style should be changed to enhance the performance of the user;
   changing the coaching style if it is determined that the coaching style should be changed to enhance the performance of the user;
   continuing with the coaching style if it is determined that the coaching style should not be changed; and
   providing feedback to the user during the workout session based on the coaching style.

2. The method of claim 1, wherein the mobile device worn by the user comprises a smartwatch.

3. The method of claim 1, wherein the feedback is provided to the user via the mobile device worn by the user.

4. The method of claim 1, wherein the data obtained from the user via the mobile device worn by the user further comprises sensor data selected from the group consisting of: a temperature of the user, sleep data from the user, user movement data, and combinations thereof.

5. The method of claim 1, wherein the data obtained from the user via the mobile device worn by the user further comprises environmental data selected from the group consisting of: outside temperature, humidity, wind speed, and combinations thereof.

6. The method of claim 1, further comprising the steps of:
   obtaining the data from the user at a beginning of the workout session via the mobile device worn by the user;
   performing a weighted evaluation of the factors that affect the performance of the user; and
   changing the coaching style for a single workout session based on the weighted evaluation.

7. The method of claim 1, further comprising the step of:
   comparing health and fitness of the user to health and fitness data of the at least one other user to determine the coaching style for the user.

8. The method of claim 1, further comprising the step of:
   obtaining updated data from the user; and
   selecting the different coaching style based on the updated data obtained from the user.

9. The method of claim 1, further comprising the step of:
   selecting the different coaching style randomly.

10. The method of claim 1, further comprising the step of:
    setting a limit on a number of attempts to select the different coaching style.

11. The method of claim 10, further comprising the step of:
    defaulting to the coaching style once the limit has been reached.

12. The method of claim 1, wherein the input from the user comprises at least one of a fitness goal of the user, and a current fitness level.

13. The method of claim 1, further comprising the step of:
    querying the user as to whether a change in the coaching style is needed to have an effective workout.

14. A computer program product for motivational coaching of a user during workout sessions, the computer program product comprising a non-transitory computer readable storage medium having program instructions embodied therewith, the program instructions executable by a computer to cause the computer to:
    select a coaching style for the user based on input from the user and from coaching styles used for at least one other user;
    query the user as to whether the user approves of the coaching style selected for the user;
    select a different coaching style if the user disapproves of the coaching style selected for the user;
    determine, during a workout session, whether the coaching style should be changed to enhance performance of the user based on data obtained from the user via a mobile device worn by the user, wherein the mobile device worn by the user comprises at least an EDA sensor that collects the data from the user in real-time indicating a level of stress of the user, and an accelerometer and a gyroscope sensor that collect the data from the user in real-time indicating movement of the user, wherein the level of stress of the user and the movement of the user are factors that affect the performance of the user and whether the coaching style should be changed to enhance the performance of the user;
    change the coaching style if it is determined that the coaching style should be changed to enhance the performance of the user;
    continuing with the coaching style if it is determined that the coaching style should not be changed; and
    provide feedback to the user during the workout session based on the coaching style.

15. The computer program product of claim 14, wherein the mobile device worn by the user comprises a smartwatch.

16. The computer program product of claim 14, wherein the data obtained from the user via the mobile device worn by the user further comprises sensor data selected from the group consisting of: a temperature of the user, sleep data from the user, user movement data, and combinations thereof.

17. The computer program product of claim 14, wherein the data obtained from the user via the mobile device worn by the user further comprises environmental data selected from the group consisting of: outside temperature, humidity, wind speed, and combinations thereof.

18. The computer program product of claim 14, wherein the program instructions further cause the computer to:
obtain the data from the user at a beginning of the workout session via the mobile device worn by the user;
perform a weighted evaluation of the factors that affect the performance of the user; and
change the coaching style for a single workout session based on the weighted evaluation.

* * * * *